United States Patent [19]

Rogge et al.

[11] Patent Number: 4,663,959
[45] Date of Patent: May 12, 1987

[54] METHOD AND DEVICE FOR CALIBRATING TRANSDUCERS FOR DETERMINING GAS CONCENTRATIONS

[75] Inventors: Bernd Rogge, Scharbeutz; Klaus Kaross; Hans-Jürgen Busack, both of Lübeck; Mihail Lungu, Reinfeld, all of Fed. Rep. of Germany

[73] Assignee: Drägerwerk Aktiengesellschaft, Lübeck, Fed. Rep. of Germany

[21] Appl. No.: 833,358

[22] Filed: Feb. 25, 1986

[30] Foreign Application Priority Data

Feb. 26, 1985 [DE] Fed. Rep. of Germany ....... 3506731

[51] Int. Cl.$^4$ ............................................. G01M 3/00
[52] U.S. Cl. ..................................................... 73/1 G
[58] Field of Search ......................... 73/1 G; 204/403; 436/136, 66, 88, 11; 128/635

[56] References Cited

U.S. PATENT DOCUMENTS

| | | | |
|---|---|---|---|
| 4,116,336 | 9/1978 | Sorensen et al. | 436/11 |
| 4,151,108 | 4/1979 | Sorensen et al. | 436/11 |
| 4,266,941 | 5/1981 | Sullivan | 73/1 G |
| 4,269,684 | 5/1981 | Zick | 73/1 G |
| 4,458,686 | 7/1984 | Clark, Jr. | 436/11 |

FOREIGN PATENT DOCUMENTS

| | | | |
|---|---|---|---|
| 0031149 | 1/1981 | European Pat. Off. | |
| 2645736 | 11/1977 | Fed. Rep. of Germany | 73/1 G |
| 0607131 | 5/1978 | U.S.S.R. | 73/1 G |

OTHER PUBLICATIONS

American Heritage Dictionary, 1982.

Primary Examiner—Stewart J. Levy
Assistant Examiner—Robert R. Raevis
Attorney, Agent, or Firm—Walter Ottesen

[57] ABSTRACT

A method is disclosed for calibrating transducers for determining gas concentrations, in particular for the transcutaneous measurement of blood gases. In the method, the testing chamber is exposed on its measuring surface, through an overlay, to a known gas concentration. The method provides for a simpler application of the calibration medium to the measuring surface of the transducer, such that an overlay provided with substances required for furnishing the known gas concentration is applied directly onto the measuring surface of the testing chamber, covering it. An overlay is also disclosed and is embodied as a paper strip having two impregnated zones, separated from one another by an intermediate piece provided with a coating.

14 Claims, 3 Drawing Figures

METHOD AND DEVICE FOR CALIBRATING TRANSDUCERS FOR DETERMINING GAS CONCENTRATIONS

FIELD OF THE INVENTION

The invention relates to a method for calibrating transducers for determining gas concentrations, in particular for transcutaneous measurement of blood gases, in which the testing chamber is exposed on its measuring surface to a known gas concentration through an overlay. An overlay for performing the calibrating method is also described.

BACKGROUND OF THE INVENTION

A method of this type is known from German Pat. No. 26 45 736.

In this patent, to calibrate a transducer using a suitable calibration solution, such as water or sodium sulfite, an overlay is provided which is adapted to the measuring surface of the transducer. The overlay has a calibration volume, which must be positioned exactly over the measuring surface. The calibration solution is introduced into this calibration volume, retained there and then removed once again. The overlay comprises an adhesive layer, for example, and a covering layer disposed over it; a felt-like inlay may be provided in the adhesive layer, which by suitable means is disposed centrally over the measuring surface in order to receive the calibration solution.

Typically, two different calibration solutions are selected for calibrating the known transducers; where a transducer for transcutaneous determination of the oxygen content of blood is to be calibrated, these solutions are pure water and a solution of sodium sulfite in liquid or paste form. In both cases, care must be taken that the appropriate calibration volumes be disposed exactly above the measuring surface, using localizing rings provided to that end. Air bubbles must be prevented from forming in the calibration solutions introduced into the calibrating volumes, and the calibration volumes must cover the measuring surface completely during the entire calibration procedure. Because of these requirements, the transducer must be supported in a prescribed way during the calibration procedure. Transducers for transcutaneous determination of the blood oxygen content, for example, can accordingly be calibrated by the known method only in a horizontal position.

Preparing the calibration solutions also necessitates further handling steps, which must be performed before the calibration itself is done. Specifically, the required calibration solutions must first be mixed according to specific prescriptions, and the shelf life of the mixed solutions is limited. To prepare a suitable sodium sulfite solution, for instance, first a specific amount of sodium sulfite must be dissolved in pure water, and then it must be introduced drop by drop into the calibrating volume, using additional equipment such as pipettes. Once the sodium sulfite solution has been prepared, it cannot be held for a relatively long period; instead, typically after a period of a month, it must be discarded and prepared anew.

Once calibration has been performed, both the calibration solution and the retaining rings used to center the calibration volume must be removed, and any residues of the calibration solution must be particularly carefully removed from the measuring surface.

European Pat. application No. EP-A-31 149 does teach that the usability of calibration solutions, in particular sodium sulfite, can be indicated from the shift in the pH value by means of a suitable color indicator, and that the calibration solution can be discarded as unusable after a certain threshold pH value is attained, as determined by the color change, for instance from blue to yellow. However, this does not spare the user the work of mixing a new solution, which again has only limited shelf life, once a given calibration solution has become unusable.

Furthermore, if even slight amounts of weak acids or alkalis are present in the calibration solution due to oversight, the result is an uncontrolled shift in the pH value, which means that a direct correlation between a color change and the usability or nonusability of the calibration solution can no longer be made.

SUMMARY OF THE INVENTION

It is an object of the invention to provide an improved method of the above type such that the calibration solution is prepared, ready for use, in only the small quantity needed for a single calibration, immediately prior to the calibration procedure, and that the calibration solution can be applied to the measuring surface by means of the overlay without using additional tools, and a calibration volume need not be accurately centered over the measuring surface.

This object is attained according to a feature of the invention in that an overlay, provided with the substances required for providing the known gas concentration, is applied directly onto the measuring surface of the testing chamber, covering it. A suitable overlay for performing the method may be a porous strip provided with the required substances and capable of being wetted with the solvent. The overlay may be provided in the form of an impregnation or a coating with the soluble substance.

The shelf life of the overlay provided with the substance is unlimited as compared with the calibration solution which is only briefly stable. Because the overlay is applied directly to the measuring surface, the substance required for calibration is in surface contact with the measuring surface and additional equipment is not needed for applying it or centering it there.

In a further feature of the invention, it is provided that the overlay be made absorbent in a known manner and provided with soluble substances, and then saturated with a solvent prior to being applied to the measuring surface. Since the overlay, once it has been saturated with solvent, represents a closed film of calibration solution, having a large surface area, its absorbency and porosity mean that it will store a quantity of calibration solution sufficient for performing the calibration. By means of the saturated overlay, a moisture film is produced over the entire measuring surface, covering this surface completely with the calibration solution without forming air bubbles or similar disturbances, even on hydrophobic membranes such as are typically used for sealing the measuring surface. Because of how this moisture film is embodied, the overlay continues to adhere to the measuring surface in every conceivable position of the transducer, because of the forces of adhesion; thus, the calibration procedure can be performed no matter what the position of the transducer. Once the calibration procedure is completed, the overlay is removed by sliding it off the measuring surface, which does not damage the measuring surface; at the same time, all the residues of the calibration solution are wiped away as well. No additional cleaning operation need be performed later.

If a zero calibration is to be performed, the overlay should advantageously be impregnated with sodium sulfite. This impregnation can suitably be done with a 70% to 100% saturated sodium sulfite solution, and after the evaporation of the solvent, sodium sulfite is present in the overlay in solid form. Sodium sulfite is known to act as an oxygen-consuming agent, so that the oxygen in the air does not pass through the saturated overlay to the measuring surface.

As the second calibration step, in addition to zero calibration, a calibration is performed with the oxygen in the air. Since the water vapor contained in the air can lead to a false calibration value, it is desirable to use dry calibration gas. By additionally impregnating or coating the overlay with silica gel as an additional substance, the water vapor that diffuses onto the dry overlay is kept out of the air. Thus an additional correction for water vapor is no longer necessary.

If a calibration of a transducer for transcutaneous determination of $CO_2$ is to be performed, the overlay is suitably provided with a substance containing carbonate.

To activate the impregnated substance so that it will release the calibration gas, water can be used, on which no special cleanliness requirements are imposed, in contrast to known calibration solutions. If required, even weak acids or bases can be used as solvents, without impairing the effectiveness of the calibration solution.

According to a particularly simple feature of the invention, a strip of porous material, such as paper that can be wetted by the solvent, can be used for the overlay for performing the method of calibrating transducers for determining gas concentrations. This overlay is provided with a substance that, after the paper strip has been wetted with a suitable solvent, produces the known gas concentration required for the calibration. If sodium sulfite, for example, is used as an impregnated substance according to the method steps, and if this substance is dissolved in water, for example, then a paper strip is obtained which when applied to the measuring surface of the transducer generates an oxygen-free gas concentration over the measuring surface. A zero calibration of the transducer is thus effected in a particularly simple manner.

For easier manipulation, the paper strip may be partly provided with a coating on which the strip can be grasped so that the strip can be applied to the measuring surface of the transducer.

In a particularly favorable manner, the paper strip can be made up of a plurality of adjacent layers, either resting directly on one another or, as needed, joined together by means of a suitable interlay, for instance to increase the adhesion of the layers to one another. A first layer is impregnated with sodium sulfite, for instance, and a second layer with silica gel in order to inhibit water vapor.

To perform several calibration procedures in succession with various gas concentrations, in a further embodiment of the invention, the paper strip can be divided into a plurality of zones, each impregnated with different substances for furnishing the known gas concentrations that are required.

For instance, a first zone for zero calibration of a transducer for measuring oxygen can be impregnated with sodium sulfite and a second zone for generating a known $CO_2$ concentration, for calibrating a transducer for $CO_2$ measurement, can be impregnated with a substance containing carbonate. Prior to the calibration procedure, both zones can be saturated with the same solvent, such as water, so as to furnish the known gas concentration required for the calibration.

To prevent mixing of the saturated zones that are impregnated with different substances, it is advantageous for the zones to be separated from one another by an intermediate element, which for instance is not wettable by the solvent and is neutral to the substances used.

To perform the method, it has proved to be particularly favorable for the paper strips to be made no thinner than approximately 0.2 mm to 1 mm. This provision, for instance when a zero calibration is performed by means of impregnated and dissolved sodium sulfite, prevents the diffusion of oxygen from the atmosphere through the saturated paper strip to the measuring surface of the transducer during the calibration procedure.

It will be readily apparent that such a paper strip can be ready-made in any arbitrary known manner to facilitate its handling. For instance, for removal of a calibration strip provided for calibration, the strip can be wound up on a roll into a plurality of successive individual strips, which in turn are easily separated from one another by means of a suitable perforation.

The embodiment of the paper strips can be adapted to the various shapes of the measuring surfaces of transducers by means of appropriate pattern pieces.

For larger transducers, which for calibration must have a larger quantity of gas in a known gas concentration, the paper strip can be provided in a thicker version with a larger surface area, so that the required amount of substance can be applied and dissolved in the appropriate solvent.

BRIEF DESCRIPTION OF THE DRAWING

The invention will now be described with reference to the drawing wherein.

DESCRIPTION OF THE PREFERRED EMBODIMENTS OF THE INVENTION

Figure 1:
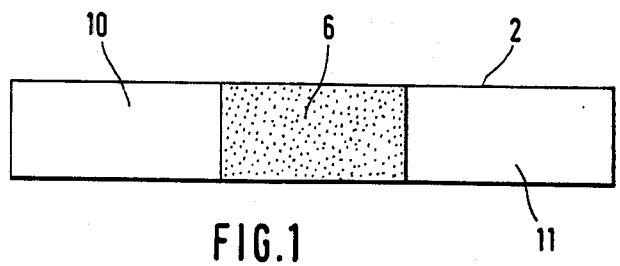
FIG. 1 is a plan view of the overlay according to an embodiment of the invention.
Figure 2:
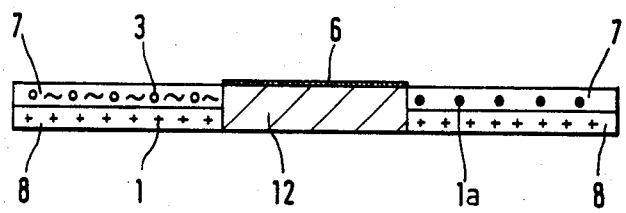
FIG. 2 is a section taken through the overlay of FIG. 1.

In FIG. 1, the overlay 2 is shown and includes two impregnated zones 10, 11 and a hydrophobic intermediate piece 12 disposed between the impregnated zones; the intermediate piece 12 has a coating 6 for easier handling of the overlay 2 embodied as a paper strip. A paper strip 2 which has been prepared for performing the $O_2$ zero calibration is shown in section in FIG. 2. Each zone 10, 11 is divided into two layers 7, 8. The layer 7 of the zone 10 contains an impregnation of sodium sulfite (represented by wavy lines) which has been dissolved in a solvent 3 (represented by clear circles). The layer 8 in both zones 10, 11 is impregnated with silica gel (represented by crosses), as the substance 1. The layer 7 of zone 11 contains a carbonate-containing substance 1a (indicated by dots). The intermediate piece 12 is disposed between the two zones 10 and 11 and prevents the dissolved substances 1a from the two zones 10 and 11 from mixing with one another.

Figure 3:
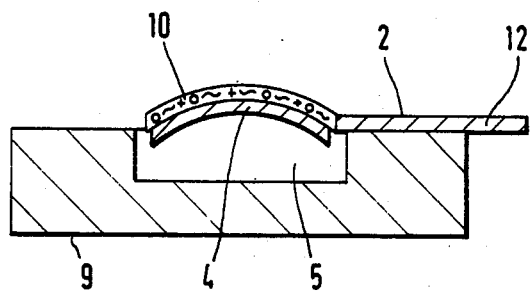
FIG. 3 shows a cut overlay on the measuring surface of the transducer.

FIG. 3 shows a paper strip 2, the zone 10 of which has been applied to the measuring surface 4 of the measuring chamber 5 of a transducer 9. The zone 10 comprises only one layer, which along with the impregnation of sodium sulfite additionally contains an impregnation of silica gel. The intermediate piece 12, embodied as an end piece, is located outside the vicinity of the measuring surface 4 and serves to apply the paper strip 2 to the measuring surface 4 and to remove it again therefrom.

To perform a calibration with dried oxygen from the air, the dry paper strip 2 is placed upon the measuring surface 4, so that the oxygen from the air passes through the layer to the measuring surface 4. The water vapor is inhibited from passing through by the silica gel.

In the ensuing zero calibration, the layer is saturated with water, causing the sodium sulfite to become dissolved and binding the oxygen that has diffused from the air through the layer.

It is understood that the foregoing description is that of the preferred embodiments of the invention and that various changes and modifications may be made thereto without departing from the spirit and scope of the invention as defined in the appended claims.

What is claimed is:

1. A method for calibrating a transducer for determining transcutaneous gas concentrations, said transducer having a measuring surface, the method comprising:
    obtaining an absorbent overlay comprising a soluble calibration substance capable of providing a known gas concentration;
    covering the measuring surface of the transducer with said overlay;
    saturating the overlay with a solvent prior to covering the measuring surface of the transducer; and,
    calibrating the transducer.

2. The method of claim 1, wherein said substance is sodium sulfite for forming a $O_2$-zero calibration solution.

3. The method of claim 2, said overlay containing silica gel as a further substance for inhibiting water vapor.

4. The method of claim 1, said overlay being provided with a carbon-containing substance to form a known concentration of carbon dioxide.

5. The method of claim 1, wherein said solvent is water.

6. The method of claim 1, said overlay being provided with sodium sulfite in the form of a 70% to 100% saturated solution of sodium sulfite in a solvent.

7. An overlay for use in calibrating a transducer for determining transcutaneous gas constructions, the transducer having a measuring surface, the overlay comprising:
    a porous strip capable of being placed directly onto and covering said measuring surface;
    a substance contained in said strip for providing a known gas concentration; and,
    said strip being wettable by a solvent for coacting with said substance to provide the known gas concentration for calibration.

8. The overlay of claim 7, comprising a coating over a portion of said strip to facilitate manipulation thereof.

9. The overlay of claim 7, said strip comprising a plurality of mutually adjacent layers; and, the overlay further comprising a plurality of substances contained in corresponding ones of said layers for providing respective known gas concentrations.

10. The overlay of claim 9, a first one of said layers containing sodium sulfite as a substance therein for providing a zero concentration; and, a second one of said layers containing silica gel as a substance for inhibiting water vapor from the gas.

11. The overlay of claim 7, said strip comprising a plurality of mutually adjacent zones arranged along the length thereof; and, a plurality of substances contained in said zones for providing known gas concentrations.

12. The overlay of claim 11, a first one of said zones containing sodium sulfite as a substance therein for providing a zero-calibrating solution; and, a second one of said zones containing a carbon-containing substance for providing known $CO_2$-concentration.

13. The overlay of claim 11, comprising an intermediate piece for separating two mutually adjacent zones from each other.

14. The overlay of claim 7, said strip having a thickness of approximately 0.2 mm to 1.0 mm.

* * * * *